(12) United States Patent
Navsariwala et al.

(10) Patent No.: US 7,309,982 B2
(45) Date of Patent: Dec. 18, 2007

(54) PORTABLE SYSTEM FOR RAPID CHARACTERIZATION OF ELECTRICAL PROPERTIES OF A MATERIAL

(75) Inventors: Umesh D. Navsariwala, Schaumburg, IL (US); Nicholas E. Buris, Deer Park, IL (US); Edward C. Porrett, Schaumburg, IL (US); William J. Turney, Schaumburg, IL (US)

(73) Assignee: Motorola, Inc., Schaumburg, IL (US)

( * ) Notice: Subject to any disclaimer, the term of this patent is extended or adjusted under 35 U.S.C. 154(b) by 191 days.

(21) Appl. No.: 11/287,661

(22) Filed: Nov. 28, 2005

(65) Prior Publication Data

US 2007/0120562 A1   May 31, 2007

(51) Int. Cl.
*G01N 27/72* (2006.01)
*G01R 33/12* (2006.01)

(52) U.S. Cl. .................. 324/228; 324/244; 324/260

(58) Field of Classification Search ........... 324/228, 324/230, 244, 260
See application file for complete search history.

(56) References Cited

U.S. PATENT DOCUMENTS 4,222,267 A * 9/1980 Aldrich .................. 73/304 C

2007/0046289 A1 * 3/2007 Troxler ..................... 324/334

OTHER PUBLICATIONS

Marsland, et al., Dielectric Measurements with an Open-Ended Coaxial Probe, IEE Proceedings, vol. 134, Pt. II, No. 4, Aug. 1987, pp. 341-349.

* cited by examiner

*Primary Examiner*—Bot LeDynh

(57) ABSTRACT

A material properties detection system (100). The system can include an antenna (120) that is tuned for operation within a frequency band over which the antenna transmits. The system also can include a transmitter (210) that generates electromagnetic energy across the frequency band and forwards the electromagnetic energy to the antenna. An impedance measurement circuit (215) can be provided. The impedance measurement circuit can measure an input impedance of the antenna over the frequency band and generate measured impedance data (225). The system can include a material characterization application (230) that processes the measured impedance data to generate a material characterization for a structure (110) to which the antenna is proximate. The material characterization can include a dielectric constant, a permittivity, a loss tangent and/or a permeability.

20 Claims, 4 Drawing Sheets

FIG. 1
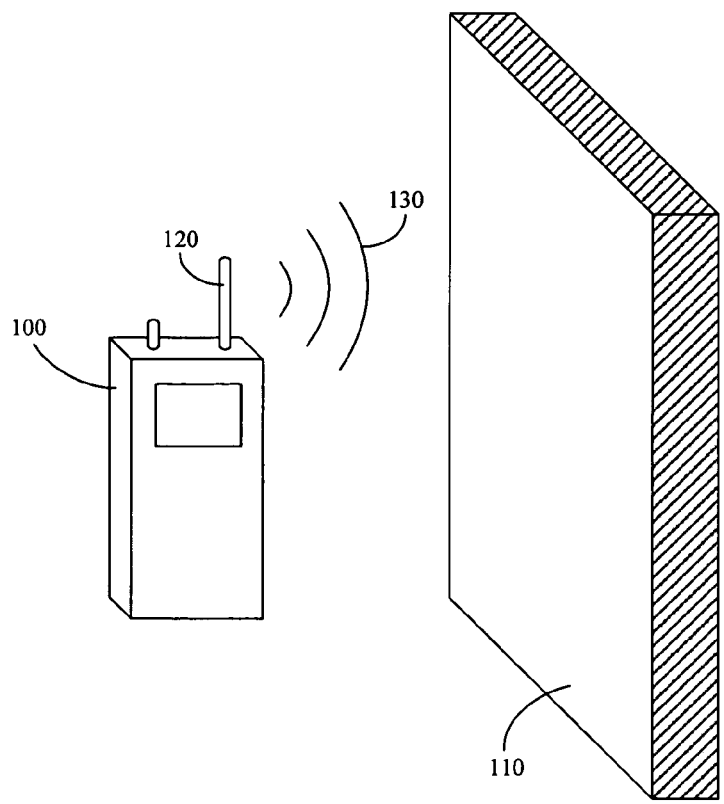
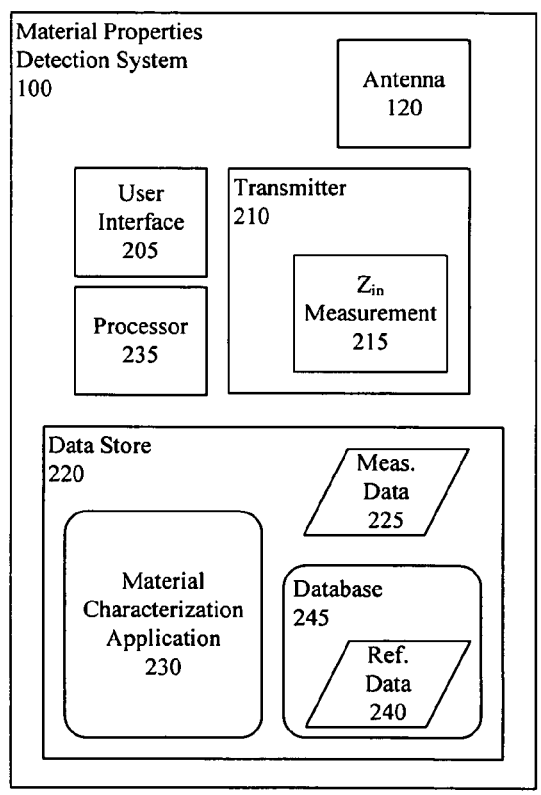
FIG. 2

PORTABLE SYSTEM FOR RAPID CHARACTERIZATION OF ELECTRICAL PROPERTIES OF A MATERIAL

BACKGROUND OF THE INVENTION

1. Field of the Invention

The present invention generally relates to characterization of material properties and, more particularly, to characterization of a material's electrical properties.

2. Background of the Invention

In order to conserve battery life, today's mobile communication devices transmit RF signals at relatively low power levels. Moreover, these devices typically transmit at frequencies in the upper MHz range (e.g. 900 MHz) or lower GHz range (e.g. 1.8 GHz). RF signals transmitted at these frequencies are especially susceptible to the influences of nearby structures, for instance walls and roofs of buildings. In particular, materials from which the structures are made often attenuate and scatter the RF signals, thus degrading signal propagation characteristics. Such signal degradation should be considered when determining transceiver locations for a wireless communication system.

The effect of a single homogenous material on an RF signal is typically determined by the electrical characteristics of the material, for instance the materials dielectric constant and loss tangent. However, structures are rarely constructed from a single homogenous material, and the electrical characteristics of different structural materials can vary greatly. For example, the electrical characteristics of concrete are different than the electrical characteristics of aluminum, wood or fiberglass insulation. Further, the electrical characteristics of a material can vary according to density variations within the material. Thus, it is difficult to estimate the true effect of a building on RF signal propagation, and typical assumptions can lead to poor system design.

Coaxial probes and other probes having short antennas or open ended cavities have been used to measure electrical properties of particular materials. However, such probes are limited in their ability to penetrate a material and generally only measure the material's outer layers. Use of data generated by these probes can lead to erroneous calculations when a structure being measured comprises multiple layers of different materials or when there are variations in material density.

SUMMARY OF THE INVENTION

The present invention relates to a material properties detection system. The system can include an antenna that is tuned for operation within a frequency band over which the antenna transmits. The system also can include a transmitter that generates electromagnetic energy across the frequency band and forwards the electromagnetic energy to the antenna.

An impedance measurement circuit can be provided. The impedance measurement circuit can measure an input impedance of the antenna over the frequency band and generate measured impedance data. The system can include a material characterization application that processes the measured impedance data to generate a material characterization for a structure to which the antenna is proximate. The material characterization can include a dielectric constant, a permittivity, a loss tangent and/or a permeability. The system also can include a data base in which reference impedance data is stored. The reference impedance data also can be processed by the material characterization application to generate the material characterization.

In one arrangement the system further can include a material properties detector and a processing system. In this arrangement, the antenna, the transmitter and the impedance measurement circuit can be components of the material properties detector. The material properties detector also can include a communication adapter through which the measured impedance data is propagated to the processing system. For example, the communication adapter can be a wireless adapter. The material characterization circuit can be a component of the processing system. The processing system also can include the data base in which the reference impedance data is stored.

The present invention also relates to a method of detecting material properties. The method can include placing an antenna proximate to a structure. The antenna can tuned to operate in a frequency band over which the antenna transmits. Electromagnetic energy can be forwarded to the antenna. The electromagnetic energy can be generated across the frequency band. An input impedance of the antenna can be measured over the frequency band and measured impedance data can be generated. The measured impedance data can be processed to generate a material characterization for the structure. For instance, a dielectric constant, a permittivity, a loss tangent and/or a permeability for the structure can be generated. In one arrangement, the measured impedance data can be forwarded from a material properties detector to a processing system. For example, the measured impedance data can be wirelessly transmitted from a material properties detector to a processing system.

The method also can include processing reference impedance data to generate the material characterization. Processing the measured impedance data can include applying a best fit algorithm to the measured impedance data to generate an impedance curve, and reference impedance data that closely matches the generated impedance curve can be selected. A resonant frequency of the measured impedance data can be identified, and a frequency offset between the resonant frequency of the measured impedance data and a resonant frequency of the reference impedance data can be identified.

BRIEF DESCRIPTION OF THE DRAWINGS

Preferred embodiments of the present invention will be described below in more detail, with reference to the accompanying drawings, in which:

FIG. 1 depicts a material properties detection system that is useful for understanding the present invention.

FIG. 2 depicts a block diagram of the material properties detection system.

DETAILED DESCRIPTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

FIG. 1 depicts a portable material properties detection system (hereinafter "system") 100 that rapidly characterizes electrical properties of a structure 110, such as a wall, ceiling, floor or any other structure to be characterized. The system 100 can be implemented in a handheld device, thereby facilitating its use to rapidly characterize different structures within a building.

The system 100 can measure input impedance of an antenna 120 while transmitting electromagnetic energy 130 across a particular frequency band while the antenna is positioned in proximity to the structure 110. The frequency band can be any desired band of frequencies and is not limited to frequency bands that are defined for commercial purposes. In one arrangement, the antenna 120 can be placed directly against the structure 110 while the input impedance is measured. Data from the input impedance measurement then can be processed to generate material characterization information, such as the structure's bulk dielectric constant and loss tangent. One skilled in the art will appreciate that permittivity and dielectric constant (or relative permittivity) are directly proportional, and that either can be generated using the system and methods described herein. Optionally, the structure's bulk permeability also can be characterized.

Oftentimes the dielectric constant, permeability, and loss tangent of a given structure are frequency dependent. For instance, the dielectric constant may decrease and the loss tangent may increase as the measurement frequency is increased. The electromagnetic energy 130 can be transmitted in a specific frequency band of interest to obtain data representing the characteristics of the structure 110 at that frequency. For example, if the structure 110 is a wall of a building in which mobile stations will be transmitting in the 900 MHz frequency band, the system 100 can transmit the electromagnetic energy 130 in the same frequency band.

Figure 3:
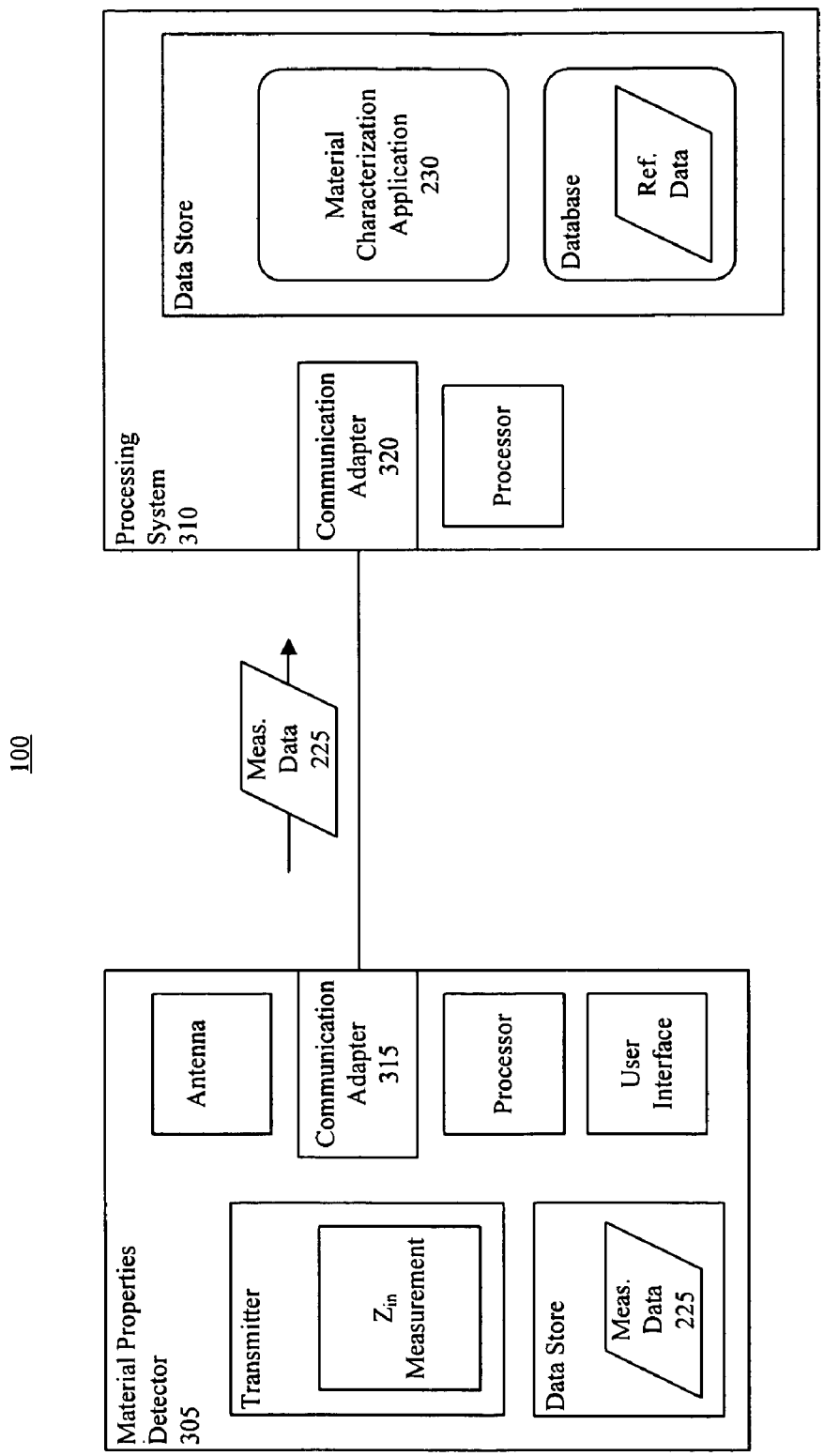
FIG. 3 depicts a block diagram of another embodiment of the material properties detection system.

FIG. 2 is a block diagram of the system 100 wherein components of the system 100 are contained in a single device. The device can be an application specific device, or a device that performs other functions. For example, the system 100 can be included in a mobile communication device. In another arrangement, various aspects of the system 100 can be implemented in different devices. For instance, referring to FIG. 3, the system 100 can include a material properties detector 305 that generates measured data 245 and a processing system 310, such as a computer, that executes a material characterization application 230 to processes the measured data 245. In this arrangement the material characterization information can be imported into another application that is executable on the processing system 310. For example, the material characterization application can be instantiated at the behest of the other application.

The material properties detector 305 can forward the measured data 225 to the processing system 310 via a cable, a wireless communication link, or in any other suitable manner. The material properties detector 305 and the processing system 310 each can include a respective communication adapter 315, 320 to support such communications. The communication adapters 315, 320 can be, for example, universal serial bus (USB) adapters, IEEE-1394 (FireWire) adapters, wired or wireless network adapters, RF transceivers, or any other suitable communication adapters. In another arrangement, the measured data 225 can be transferred from the material properties detector 305 to a removable storage device (not shown), such as a USB flash drive, and later transferred from the removable storage device to the processing system 310.

Referring again to FIG. 2, the system 100 now will be described. The system 100 can include a user interface 205 for receiving user inputs and presenting information to the user. For example, the user interface 205 can include a display, a keypad, buttons, soft-keys, a voice recognition system, and/or any other systems or devices which can be used by the user to interact with the system 100.

The system also can include a processor 235. The processor 235 can include a central processing unit (CPU), a digital signal processor (DSP), an application specific integrated circuit (ASIC), a programmable logic device (PLD), a plurality of discrete components that cooperate to process data, and/or any other suitable processing device.

As noted, the system 100 can include the antenna 120. The antenna 120 can be tuned for operation in a frequency band over which the antenna transmits. For instance, the antenna can have one or more dimensions that are approximately equal to one-half of a wavelength of the electromagnetic energy being generated by the antenna 120. Such an arrangement enables the electromagnetic energy to penetrate deeper into the structure in comparison to the use of a smaller antenna. Accordingly, structures that have multiple layers of differing materials can be accurately characterized.

For example, if the antenna 120 is a rectangular patch antenna, one or more sides of the patch antenna can have a length that is approximately one-half of the wavelength. If the antenna 120 is a whip antenna, the length of the whip can be approximately one-half of the wavelength. In one arrangement, the length can be adjustable so that the antenna 120 can be tuned for optimal operation at multiple frequencies. The antenna 120 can be, for example, a resonant one-wavelength loop antenna, a quarter-wave monopole or a broadband spiral antenna. Still, other antennas known to the skilled artisan can be used and the invention is not limited in this regard.

The system 100 also can include a transmitter 210 that generates the electromagnetic energy and forwards the electromagnetic energy to the antenna 120. In one arrangement the transmitter 210 can be a transmitter that only transmits signals. In another arrangement, the transmitter 210 also can receive signals. For instance, the transmitter 210 can be a transceiver. The transmitter 210 can generate electromagnetic energy across the frequency band in which the antenna 120 operates.

The transmitter can include an impedance measurement circuit 215 that measures the input impedance of the antenna 120 while the transmitter 210 supplies electromagnetic energy to the antenna 120. In one embodiment the impedance measurement circuit 215 can measure the input impedance using scattering parameters (S parameters), for example by measuring the input reflection coefficient ($S_{11}$). However, the invention is not limited in this regard and other methods for measuring the input impedance can be used. The impedance measurement circuit 215 can be implemented as hardware, or as a combination of hardware and software or firmware. For instance, the impedance measurement circuit 215 can be implemented using a directional coupler and a gain/phase integrated circuit (IC). Nonetheless, a myriad of other types of system components can be used to measure the input impedance of the antenna 120, and such components are within the scope of the present invention.

The system 100 also can include a data store 220 to which measured input impedance data (hereinafter "measured data") 225 can be stored. The material characterization application 230 also can be contained on the data store 220. In operation, the material characterization application 230 can be executed by a processor 235 to generate material characterization information, such as a bulk dielectric constant and a loss tangent, by processing the measured data 225. Optionally, a bulk permeability value can be generated by processing the measured data 225.

The material characterization application 230 can generate the material characterization information for the measured data 225 in any suitable manner. For example, the material characterization application 230 can compare the measured data 225 to reference data 240 and, based on the comparison, generate the material characterization information. The reference data 240 can be, for instance, a plurality of input impedance data sets stored in a data base 245 accessible to the material characterization application 255. Each data set can be generated by measuring the input impedance of the antenna 120, or an antenna equivalent to the antenna 120, with the antenna proximate to a material having known electrical characteristics. For example, a first data set can be generated with the antenna 120 proximate to a first material having a first dielectric constant and a first loss tangent. The first dielectric constant and the first loss tangent can be associated with the first data set as parameter values of the first data set. A second data set can be generated with the antenna 120 proximate to a second material having a second dielectric constant and a second loss tangent, and the second dielectric constant and second loss tangent can be associated with the second data set as parameter values of the second data set. Data sets also can be generated using other known methods, for instance using simulations, data interpolation, or other known measurement techniques. Any desired number of data sets can be generated.

Figure 4:
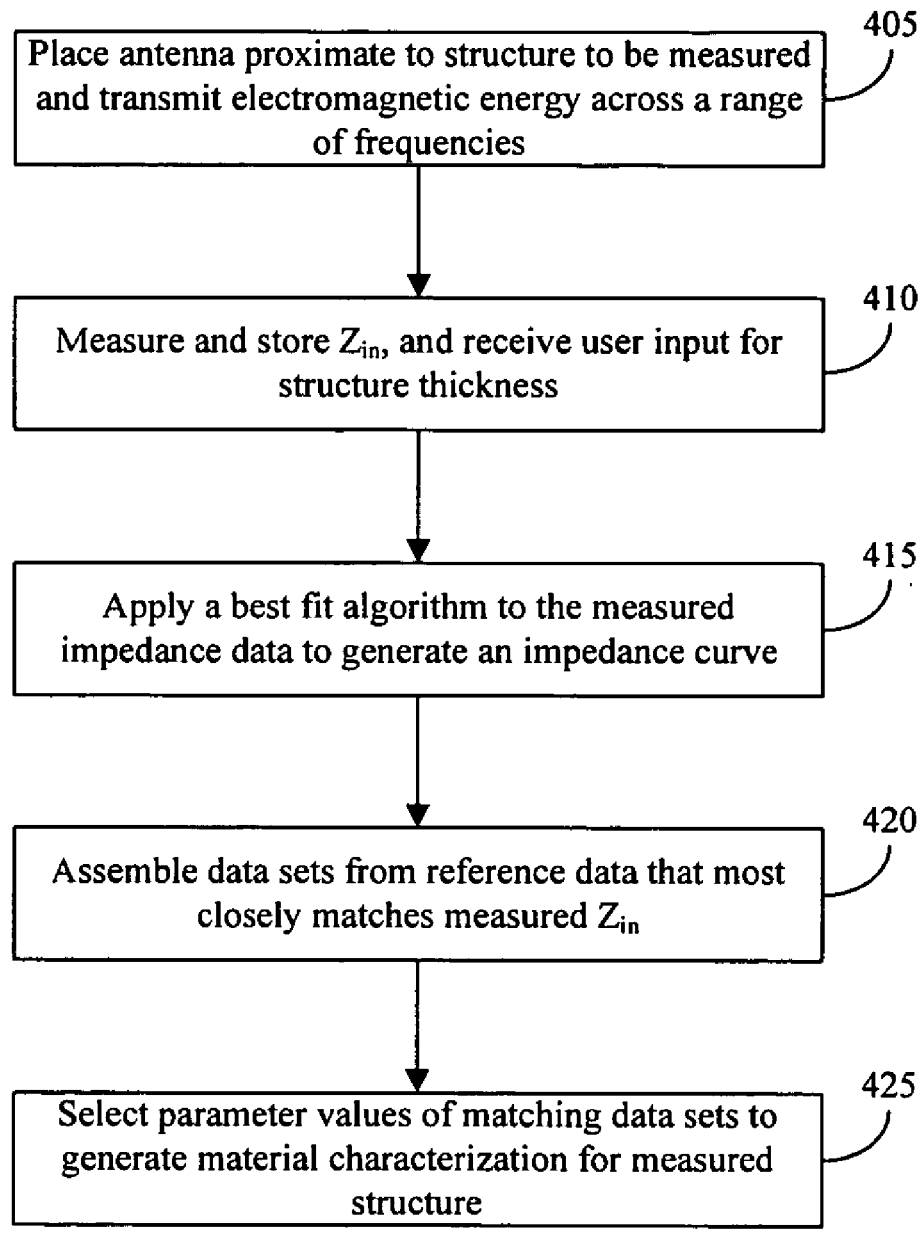
FIG. 4 is flowchart that is useful for understanding the present invention.

A flow chart useful for understanding a method 400 that can be implemented by the system 100 to characterize the structure is presented in FIG. 4. Beginning at step 405, the antenna can be placed proximate to a structure to be measured and electromagnetic energy can be transmitted through the antenna across a range of frequencies. At step 410, the input impedance of the antenna can be measured across the range of frequencies. In addition, a user input can be received for the thickness of the structure being measured.

Figure 5:
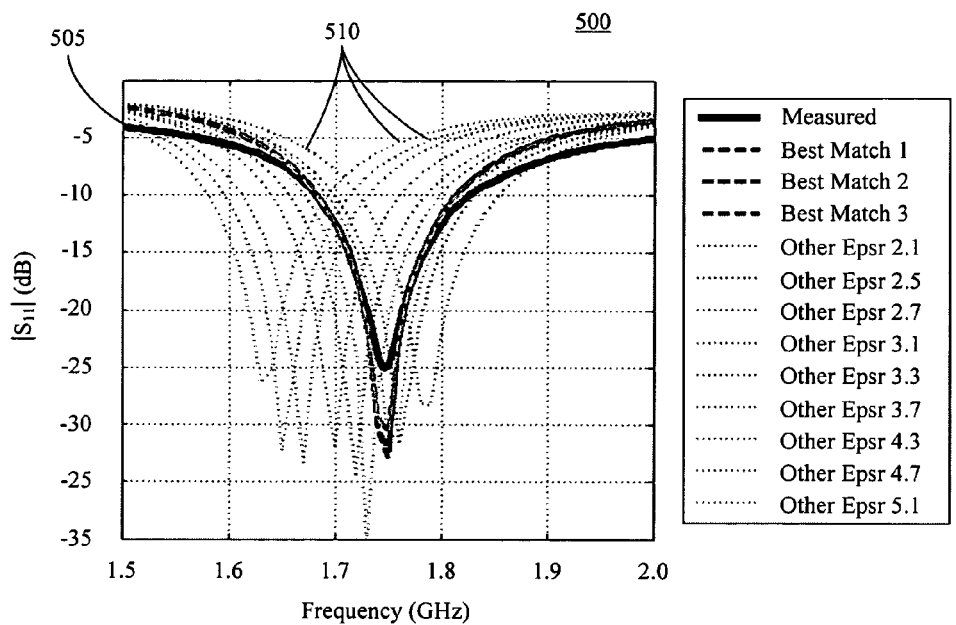
FIG. 5 is a graph of input impedance vs. frequency.

At step 415, a best fit algorithm can be applied to the measured input impedance data to generate an impedance curve. Proceeding to step 420, data sets from the reference data that most closely match the generated impedance curve can be assembled. Examples of the measured impedance curve 505 and closely matching data sets 510 are presented are presented in a graph 500 in FIG. 5. There are several methods that can be implemented for selecting the data sets that most closely match the generated impedance curve. For example, data sets which most closely match the frequency response of the generated impedance curve can be selected. In another arrangement, data sets can be selected which represent a resonant frequency that correlates to the resonant frequency of the measured data.

Figures 6, 7:
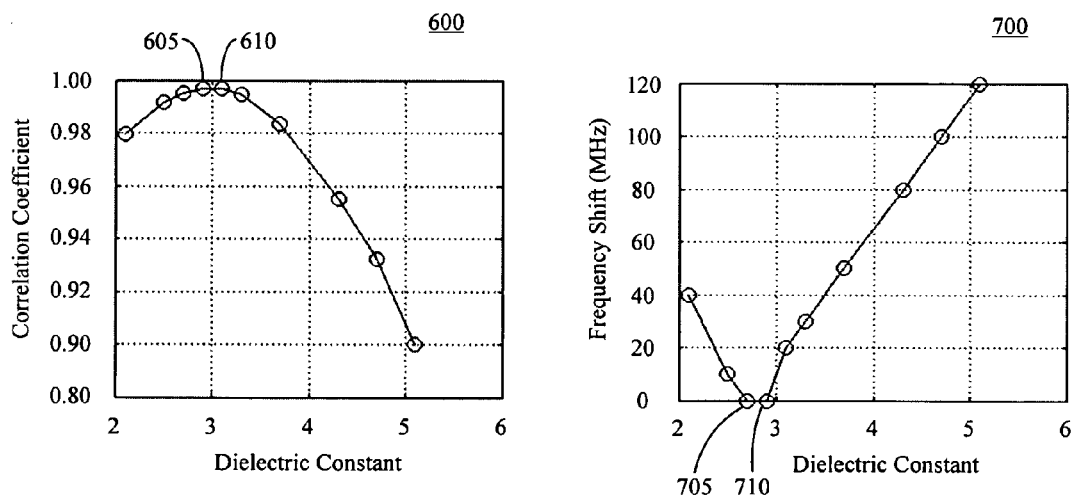
FIG. 6 is a graph of correlation coefficient vs. dielectric constant.
FIG. 7 is a graph of frequency shift vs. dielectric constant

At step 425, parameter values correlating to the matching data sets can be selected and processed to generate material characterization information for the measured structure. The bulk dielectric constant and/or permeability can be generated by selecting the values of dielectric constant and/or permeability of the most closely matching data sets, and interpolating. For example, a correlation coefficient that represents how closely a particular data set correlates to the measured data set can be assigned to each of the data sets that were previously identified. Referring to graph 600 of FIG. 6, a plot is shown of correlation coefficient vs. dielectric constant for each of the identified data sets. In the graph 600, data points 605 and 610 have the highest correlation factors, but neither has a correlation of 1.00. Accordingly, the dielectric constant values associated with the data points 605 and 610 can be interpolated to generate a net dielectric constant for the measured structure. The structure thickness can be evaluated to determine a bulk dielectric constant based on the net dielectric constant.

In another arrangement, a resonant frequency shift can be determined for each data set. The resonant frequency shift can represent the difference between the resonant frequency of the particular data set and the resonant frequency of the measured impedance data. Referring to graph 700 of FIG. 7, a plot is shown of frequency shift vs. dielectric constant for each of the identified data sets. In the graph 700, data points 705 and 710 have the lowest frequency shifts. Accordingly, the dielectric constant values associated with the data points 705 and 710 can be interpolated to generate a net dielectric constant for the measured structure.

The present invention can be realized in hardware, or a combination of hardware and software. As noted, the present invention can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a general-purpose processing system with an application that, when being loaded and executed, controls the processing system such that it carries out the methods described herein. The present invention also can be embedded in an application product, which comprises all the features enabling the implementation of the methods described herein, and which when loaded in a processing system is able to carry out these methods.

The terms "computer program", "software", "application", variants and/or combinations thereof, in the present context, mean any expression, in any language, code or notation, of a set of instructions intended to cause a system having an information processing capability to perform a particular function either directly or after either or both of the following: a) conversion to another language, code or notation; b) reproduction in a different material form. For example, an application can include, but is not limited to, a subroutine, a function, a procedure, an object method, an object implementation, an executable application, an applet, a servlet, a source code, an object code, a shared library/dynamic load library and/or other sequence of instructions designed for execution on a processing system.

The terms "a" and "an," as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically, i.e. communicatively linked through a communication channel or pathway.

This invention can be embodied in other forms without departing from the spirit or essential attributes thereof. Accordingly, reference should be made to the following claims, rather than to the foregoing specification, as indicating the scope of the invention.

What is claimed is:

1. A material properties detection system, comprising:
   an antenna tuned for operation in a frequency band over which the antenna transmits;
   a transmitter that generates electromagnetic energy across the frequency band and forwards the electromagnetic energy to the antenna;
   an impedance measurement circuit that measures an input impedance of the antenna over the frequency band and generates measured impedance data; and
   a material characterization application that processes the measured impedance data to generate a material characterization for a structure to which the antenna is proximate.

2. The system of claim 1, wherein the material characterization comprises at least one parameter selected from the group consisting of a dielectric constant, a permittivity, a loss tangent and a permeability.

3. The system of claim 1, further comprising a data base in which reference impedance data is stored, the reference impedance data also being processed by the material characterization application to generate the material characterization.

4. The system of claim 1, further comprising:
   a material properties detector; and
   a processing system;
   wherein the antenna, the transmitter and the impedance measurement circuit are components of the material properties detector and the material characterization circuit is a component of the processing system.

5. The system of claim 4, wherein the processing system further comprises a data base in which reference impedance data is stored, the reference impedance data also being processed by the material characterization application to generate the material characterization.

6. The system of claim 4, wherein the material properties detector further comprises a communication adapter through which the measured impedance data is propagated to the processing system.

7. The system of claim 6, wherein the communication adapter is a wireless adapter.

8. A material properties detector comprising:
   an antenna;
   a transmitter that generates electromagnetic energy across a frequency band and forwards the electromagnetic energy to the antenna;
   an impedance measurement circuit that measures an input impedance of the antenna over the frequency band and generates measured impedance data; and
   a communications adapter that forwards the measured impedance data to a processing system, the processing system comprising a material characterization application that processes the measured impedance data to generate a material characterization for a structure to which the antenna is proximate.

9. The system of claim 8, wherein the antenna is tuned for operation in the frequency band over which the antenna transmits.

10. The system of claim 8, wherein the material characterization comprises at least one parameter selected from the group consisting of a dielectric constant, a permittivity, a loss tangent and a permeability.

11. The system of claim 8, wherein the processing system comprises a data base in which reference impedance data is stored, the reference impedance data also being processed by the material characterization application to generate the material characterization.

12. A method of detecting material properties, comprising:
    placing an antenna proximate to a structure, the antenna being tuned over the frequency band over which the antenna operates;
    forwarding electromagnetic energy to the antenna, the electromagnetic energy being generated across the frequency band;
    measuring an input impedance of the antenna over the frequency band and generating measured impedance data; and
    processing the measured impedance data to generate a material characterization for the structure.

13. The method according to claim 12, wherein processing the measured impedance data comprises generating at least one parameter selected from the group consisting of a dielectric constant, a permittivity, a loss tangent and a permeability.

14. The method according to claim 12, further comprising forwarding the measured impedance data from a material properties detector to a processing system.

15. The method according to claim 12, further comprising wirelessly transmitting the measured impedance data from a material properties detector to a processing system.

16. The method according to claim 12, further comprising processing reference impedance data to generate the material characterization.

17. The method according to claim 16, wherein processing the measured impedance data comprises applying a best fit algorithm to the measured impedance data to generate an impedance curve.

18. The method according to claim 17, wherein processing the measured impedance data comprises selecting reference impedance data that closely matches the generated impedance curve.

19. The method according to claim 17, wherein processing the measured impedance data comprises identifying a resonant frequency of the measured impedance data.

20. The method according to claim 19, wherein processing the measured impedance data comprises identifying a frequency offset between the resonant frequency of the measured impedance data and a resonant frequency of the reference impedance data.

* * * * *